United States Patent
Wallach et al.

(10) Patent No.: US 7,056,505 B2
(45) Date of Patent: Jun. 6, 2006

(54) TNF RECEPTOR ACTION MODULATION

(75) Inventors: David Wallach, Rehovot (IL); Cord Brakebusch, Braunschweig (DE)

(73) Assignee: Yeda Research and Development Co., Ltd., Rehovot (IL)

( * ) Notice: Subject to any disclaimer, the term of this patent is extended or adjusted under 35 U.S.C. 154(b) by 656 days.

(21) Appl. No.: 10/120,397

(22) Filed: Apr. 12, 2002

(65) Prior Publication Data

US 2002/0142357 A1    Oct. 3, 2002

Related U.S. Application Data

(62) Division of application No. 08/054,970, filed on May 3, 1993, now Pat. No. 6,395,267.

(51) Int. Cl.
*A61K 39/395* (2006.01)

(52) U.S. Cl. .............................. 424/130.1; 424/142.1; 424/143.1; 530/300; 530/350; 530/387.1

(58) Field of Classification Search ................ 530/300, 530/350; 424/130.1, 142.1, 143.1
See application file for complete search history.

(56) References Cited

FOREIGN PATENT DOCUMENTS

EP    0 393 438 A3    10/1990
EP    0 444 560 A1    9/1991

OTHER PUBLICATIONS

Human TNF-R p55 and P75 from "The cytokine Facts book." (2001). Fitzgerald et al., eds., p. 478.*
Porteu et al., (1991). JBC. 266, 18846-18853.*
Aggarwal BB, "Structure of tumor necrosis factor and its receptor", *Biotherapy* 3(2):113-120 (1991).
Engelmann et al, "Antibodies to a soluble form of a tumor necrosis factor (TNF) receptor have TNF-like activity", *J Biol Chem* 265(24):14497-14504 (1990).
Espevik et al, "Characterization of binding and biological effects of monoclonal antibodies against a human tumor necrosis factor receptor", *J Exp Med* 171(2):415-426 (1990).
Hwang et al, "A 20 amino acid synthetic peptide of a region from the 55 kDa human TNF receptor inhibits cytolytic and binding activities of recombinant human tumour necrosis factor *in vitro*", *Proc R Soc Lond B Biol Sci* 245(1313):115-9 (1991).
Lie et al, "Identification of the binding site of 55kDa tumor necrosis factor by synthetic peptides", *Biochem Biophys Res Commun* 188(2):503-9 (1992).
Shalaby et al, "Binding and regulation of cellular functions by monoclonal antibodies against human tumor necrosis factor receptors", *J Exp Med* 172(5):1517-20 (1990).

* cited by examiner

*Primary Examiner*—Lorraine Spector
*Assistant Examiner*—Steven Standley
(74) *Attorney, Agent, or Firm*—Browdy and Neimark, PLLC

(57) ABSTRACT

A method of modulating signal transduction and/or cleavage in Tumor Necrosis Factor Receptors (TNF-Rs) is provided. Peptides or other molecules may interact either with the receptor itself, or with effector proteins interacting with the receptor, thus modulating the normal functioning of the TNF-Rs. Such peptides or other molecules may be employed for prophylactic and therapeutic applications in TNF associated diseases.

4 Claims, 6 Drawing Sheets

FIG. 1A

```
                                                                                  CGGCCCAGTGATCTTGA   17
18   ACCCCAAAGGCCAGAACTGGAGCCTCAGTCCAGAGAATTCTGAGAAAATTAAAGCAGAGAGGAGGGGAGAGATCACTGGGACCAGGCCGTGATCTCTATGCCCGAGTCTCAACCCTCAA   136
137  CTGTCACCCCAAGGCACTTGGGACGTCCTGGACAGACCGAGTCCCGGGAAGCCCCAGCACTGCCGCTGCCACACTGCCCTGAGCCCAAATGGGGGAGTGAGAGGCCATAGCTGTCTGGC   255

-20                                     -10                                   -1  +1
     Met Gly Leu Ser Thr Val Pro Asp Leu Leu Leu Pro Leu Val Leu Leu Glu Leu Leu Val Gly Ile Tyr Pro Ser Gly Val Ile Gly Leu
256  ATG GGC CTC TCC ACC GTG CCT GAC CTG CTG CTG CCG CTG GTG CTC CTG GAG CTG TTG GTG GGA ATA TAC CCC TCA GGG GTT ATT GGA CTG   345
      *
                         10                                     20                                  30
     Val Pro His Leu Gly Asp Arg Glu Lys Arg Asp Ser Val Cys Pro Gln Gly Lys Tyr Ile His Pro Gln Asn Asn Ser Ile Cys Cys Thr
346  GTC CCT CAC CTA GGG GAC AGG GAG AAG AGA GAT AGT GTG TGT CCC CAA GGA AAA TAT ATC CAC CCT CAA AAT AAT TCG ATT TGC TGT ACC   435

40                                     50                                  60
     Lys Cys His Lys Gly Thr Tyr Leu Tyr Asn Asp Cys Pro Gly Pro Gly Gln Asp Thr Asp Cys Arg Glu Cys Glu Ser Gly Ser Phe Thr
436  AAG TGC CAC AAA GGA ACC TAC TTG TAC AAT GAC TGT CCA GGC CCG GGG CAG GAT ACG GAC TGC AGG GAG TGT GAG AGC GGC TCC TTC ACC   525

70                                     80                                  90
     Ala Ser Glu Asn His Leu Arg His Cys Leu Ser Cys Ser Lys Cys Arg Lys Glu Met Gly Gln Val Glu Ile Ser Ser Cys Thr Val Asp
526  GCT TCA GAA AAC CAC CTC AGA CAC TGC CTC AGC TGC TCC AAA TGC CGA AAG GAA ATG GGT CAG GTG GAG ATC TCT TCT TGC ACA GTG GAC   615

100                                    110                                 120
     Arg Asp Thr Val Cys Gly Cys Arg Lys Asn Gln Tyr Arg His Tyr Trp Ser Glu Asn Leu Phe Gln Cys Phe Asn Cys Ser Leu Cys Leu
616  CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC   705

130                                    140                                 150
     Asn Gly Thr Val His Leu Ser Cys Gln Glu Lys Gln Asn Thr Val Cys Thr Cys His Ala Gly Phe Phe Leu Arg Glu Asn Glu Cys Val
706  AAT GGG ACC GTG CAC CTC TCC TGC CAG GAG AAA CAG AAC ACC GTG TGC ACC TGC CAT GCA GGT TTC TTT CTA AGA GAA AAC GAG TGT GTC   795
                                                                     Δ(170-174)
                         160                                         Δ(170-179)          Δ(175-179)            180
     Ser Cys Ser Asn Cys Lys Lys Ser Leu Glu Cys Thr Lys Leu Cys Leu Pro Gln Ile Glu Asn Val Lys Gly Thr Glu Asp Ser Gly Thr
796  TCC TGT AGT AAC TGT AAG AAA AGC CTG GAG TGC ACG AAG TTG TGC CTA CCC CAG ATT GAG AAT GTT AAG GGC ACT GAG GAC TCA GGC ACC   885

190                     S(197)A        200                                 210
     Thr Val Leu Leu Pro Leu Val Ile Phe Phe Gly Leu Cys Leu Leu Ser Leu Leu Phe Ile Gly Leu Met Tyr Arg Tyr Gln Arg Trp Lys
886  ACA GTG CTG TTG CCC CTG GTC ATT TTC TTT GGT CTT TGC CTT TTA TCC CTC CTC TTC ATT GGT TTA ATG TAT CGC TAC CAA CGG TGG AAG   975
             Δ(215-426)
                         220                                    230                                 240
     Ser Lys Leu Tyr Ser Ile Val Cys Gly Lys Ser Thr Pro Glu Lys Glu Gly Glu Leu Glu Gly Thr Thr Thr Lys Pro Leu Ala Pro Asn
976  TCC AAG CTC TAC TCC ATT GTT TGT GGG AAA TCG ACA CCT GAA AAA GAG GGG GAG CTT GAA GGA ACT ACT ACT AAG CCC CTG GCC CCA AAC   1065
```

FIG.1B

```
                Δ(244-426)
                    ▼                                                    250                                        260                                         270
           Pro Ser Phe Ser Pro Thr Pro Gly Phe Ser Pro Val Pro Ser Ser Thr Phe Ser Ser Thr Tyr Thr
1066       CCA AGC TTC AGT CCC ACT CCA GGC TTC AGT CCC GTG CCC AGT TCC ACC TTC ACC TCC AGC TCC ACC TAT ACC          1155
                                        280                                        290                                        300
           Pro Gly Asp Cys Pro Asn Phe Ala Ala Pro Arg Arg Glu Val Ala Pro Tyr Gln Gly Ala Asp Pro Ile Leu Ala Thr Ala Leu Ala
1156       CCC GGT GAC TGT CCC AAC TTT GCG GCT CCC CGC AGA GAG GTG GCA CCA TAT CAG GGG GCT GAC CCC ATC CTT GCG ACA GCC CTC GCC   1245
                                                                                                            320                                                         330
           Ser Asp Pro Ile Pro Asn Pro Leu Gln Lys Trp Glu Asp Ser Ala His Lys Pro Gln Ser Leu Asp Thr Asp Pro Ala Thr Leu Tyr
1246       TCC GAC CCC ATC CCC AAC CCC CTT CAG AAG TGG GAG GAC AGC GCC CAC AAG CCA CAG AGC CTA GAC ACT GAT GAC CCC GCG ACG CTG TAC   1335
                                           340                                        350                                        360
           Ala Val Val Glu Asn Val Pro Pro Leu Arg Trp Lys Glu Phe Val Arg Arg Leu Gly Leu Ser Asp His Glu Ile Asp Arg Leu Glu Leu
1336       GCC GTG GTG GAG AAC GTG CCC CCG TTG CGC TGG AAG GAA TTC GTG CGG CGC CTA GGG CTG AGC GAC CAC GAG ATC GAT CGG CTG GAG CTG   1425
                                           Δ(342-426)
                                               ▼                                              Δ(374-426)
                                                                                                  ▼
                                                                                       370                                        380                                        390
           Gln Asn Gly Arg Cys Leu Arg Glu Ala Gln Tyr Ser Met Leu Ala Thr Trp Arg Arg Thr Pro Arg Glu Ala Thr Leu Glu Leu
1426       CAG AAC GGG CGG TGC CTG CGC GAG GCG CAA TAC AGC ATG CTG GCG ACC TGG AGG CGG CGC ACG CCG GAG GCC ACG CTG GAG CTG          1515
                                           Δ(405-426)
                                               ▼                                              Δ(415-426)
                                                                                                  ▼
                                                                  400                                        410                                        420
           Leu Gly Arg Val Leu Arg Asp Met Asp Leu Leu Gly Leu Glu Asp Ile Glu Ala Leu Cys Gly Pro Ala Ala Leu Pro Pro Ala
1516       CTG GGA CGC GTG CTC CGC GAC ATG GAC CTG CTG GGC CTG GAG GAC ATC GAG GCG CTT TGC GGC CCC GCC CTC CCG CCC GCG          1605
           Pro Ser Leu Leu Arg End
           426
1606       CCC AGT CTT CTC AGA TGA  GGCTGCGCCCTGCGGGGCAGCTCTAAGGACCGTCCTGCCGAGATCGCCTTCCAACCCCACTTTTCTGGAAAGGAGGGGTCCTGCAGGGCAAGCA   1718
                               *
1719       GGAGCTAGCAGCCGCTTGGTGCTAACCCCTCGATGTACATAGCTTTTCTCAGCTGCCTGCGCGCCGACAGTCAGCGTCTGTGCGCGGAGAGAGGTGCGCCGTGGCTCAAG   1837
1838       AGCCTGAGTGGGTGGTTTGCGAGGATGAGGACGCTATGCCTCATGCCGTTTTGGGTGCCTCCACCAGCAAGCTGCTCGGGGCCCCTGTTCGTCCCTGAGCCTTTTTCACAGTGC   1956
1957       ATAAGCAGTTTTTTTTTTGTTTTTGTTTTGCTGTTTAAATCAATCATGTTACACTAATAAGAAACTTGGCACTCCGTGTCCCTGCCTGGACAAGCACATAGCAAGCTGAAC   2075
2076       TGTCCTAAGGCAGGGGCAGGGGCGAGCACGACGGAACAATGGGGCCTTCAGCTGTGGACTTTTGTACATACACTAAATTCTGAAGTTAAAAAAAAAAAAAAAA   2175
```

TNF RECEPTOR ACTION MODULATION

CROSS-REFERENCE TO RELATED APPLICATIONS

The present application is a divisional of U.S. application Ser. No. 08/054970, filed May 3, 1993, now U.S. Pat. No. 6,395,267, the contents being incorporated herein by reference.

FIELD OF THE INVENTION

The present invention relates to the modulation of signal transduction by the tumor necrosis factor receptors (TNF-Rs) and to modulation of the cleavage of these TNF-Rs. More particularly, the invention provides peptides and other substances which interact either with the TNF-Rs, or with effector proteins interacting with the receptor, and thus can be employed for prophylactic and therapeutic applications in diseases associated with the function of TNF.

BACKGROUND OF THE INVENTION

TNF, a pro-inflammatory cytokine produced primarily by macrophages, contributes to the defense of the host against pathogens as well as to various detrimental manifestations of inflammation through a variety of different effects on cell function (Old, 1990; Beutler and Cerami, 1989). These effects are initiated by the binding of TNF to specific, high affinity cell surface receptors (TNF-Rs), expressed on most kinds of cells (Baglioni et al, 1985; Beutler et al, 1985; Kull et al, 1985; Tsujimoto et al, 1985; Aggarwal et al, 1985; Israel et al, 1986). The receptors provide the intracellular signals for cell response to TNF (Engelmann et al, 1990a). Two molecular species of the TNF-RS, the p55 and the p75 TNF-R, expressed differentially in different types of cells, have been identified (Engelmann et al, 1990b; Brockhaus et al, 1990).

One of the most distinct characteristics of TNF compared to other immune system mediators is its ability to elicit cell death. In many severe diseases, such as autoimmune disorders, rheumatoid arthritis, graft rejection and graft-versus-host disease, TNF seems to be a major cause for pathological tissue destruction. Blocking TNF activity in these conditions is therefore of the highest importance for the development of new therapies for these diseases.

On the other hand, in certain other situations it is advantageous to augment the function of TNF, e.g., in situations where its anti-tumor or antibacterial activities are beneficial.

The main mediator for the cytotoxic effect of TNF on fibroblastoid and epithelial cells is the p55 TNF-R, which also is the prevalent TNF-R type on these cell lines. Blocking this receptor species abolishes the cytocidal effect of TNF, while inducing aggregation of the receptor molecules can mimic the cytocidal effect of TNF.

The soluble form of this receptor, as well as the soluble form of the other (p75) TNF-R, have been shown to have inhibitory effects on TNF function. Evidence was presented that these soluble forms are derived proteolytically from the cell surface forms, (Nophar et al, 1990; Porteu and Nathan, 1990; Porteu et al, 1991).

Both the signaling by the receptors and the cleavage of the receptors appear to reflect interactions between the receptor and some cellular effector proteins; the cleavage—by interacting with regulatable proteases, and the signaling—by interacting with proteins having some signaling activity.

SUMMARY OF THE INVENTION

The present invention provides a method of modulating signal transduction and/or cleavage in tumor necrosis factor receptors (TNF-Rs) comprising interfering with one or more amino acids in the sequence of a TNF-R or with an effector protein interacting with the TNF-R.

This interference influences the normal functioning of the TNF-Rs or influences an effector protein interacting therewith, and thereby modulates signal transduction by causing partial or total inhibition thereof, or influences shedding, i.e., abolishes cleavage of the soluble form of the receptor.

The present invention further provides peptides or other molecules which interact either with the receptor itself, i.e., interact with one or more amino acids in the receptor sequence, or interact with the effector proteins, and thus modulate the normal functioning of the TNF-Rs. The above molecules also include antibodies or fragments thereof.

The peptides and other substances may either be produced by conventional or by recombinant methods.

The invention also provides pharmaceutical compositions comprising the above peptides or other substances for treatment of TNF-related disorders.

BRIEF DESCRIPTION OF THE DRAWINGS

FIGS. 1A and 1B show the nucleotide (SEQ ID NO:1) and amino acid (SEQ ID NO:2) sequences of the p55 TNF receptor wherein the circled portions are the sequences of the leader and transmembrane domains and the arrows denote the mutations and deletions performed.

DETAILED DESCRIPTION OF PREFERRED EMBODIMENTS

Figure 2:
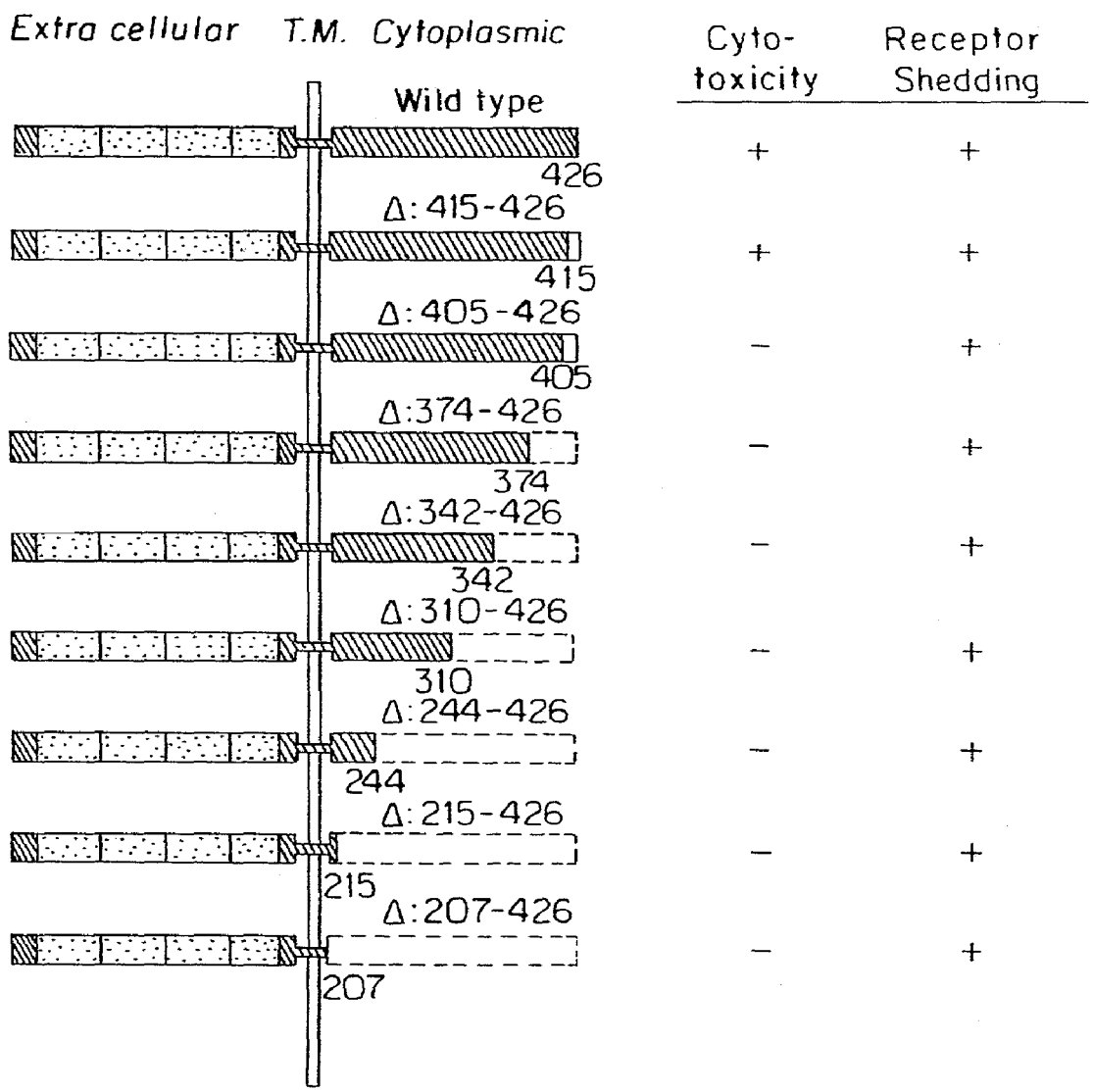
FIG. 2 illustrates various deletion mutants examined.

A short stretch of amino acids in the intracellular part of the p55 TNF receptor was identified, which was found to be essential for the triggering of cell death by TNF. Mutants of the p55 TNF-R with C-terminal deletions in the intracellular part cannot signal for the cytotoxic effect, if this stretch of amino acids was deleted. In contrast, truncated receptors containing this amino acid sequence are fully able to elicit cell death. Molecules which can specifically bind to this sequence, as well as molecules which mimic the structure of this sequence but lack its ability to stimulate cell death, can be applied as intracellular inhibitors against TNF. They will inhibit the interaction of the TNF-Rs with molecules functioning downstream in the signal transduction chain.

Moreover, a specific amino acid in the transmembrane domain of the human p55 TNF-R was identified, which is necessary to trigger the full cytotoxic effect of TNF and also plays a decisive role in the shedding of the soluble form of the receptor. Exchange of this amino acid with a "neutral" amino acid severely impairs the signaling, yet does not lead to complete inactivation of the signal transduction mechanism. It also abolishes shedding of the soluble form of the receptor. Therefore, molecules which are designed to specifically interact with this amino acid can attenuate the cytocidal activity of TNF as well as making available more receptor sites on the surface of the cells due to the inhibition of the shedding of the extra-cellular, soluble form of the receptor and, thus, will allow the use of TNF for therapeutic purposes without eliciting cell death.

Another stretch of amino acids in the region of the receptor just external to the transmembrane region was also found to be essential for cleavage of the soluble form of the receptor. Therefore, interference with this stretch, or with effector proteins interacting therewith, will also influence the functioning of the receptor.

Clones of A9 cells expressing wild type and mutant forms of the human p55 TNF-R were identified by binding of radiolabeled human TNF. Clones exhibiting approximately ten-fold enhancement of TNF binding compared to non-transfected or control-transfected, i.e., transfected only with the neomycin resistance conferring plasmid, A9 cells, were employed for further work.

Probing the sensitivity of the transfected cells to the cytocidal effect of TNF with monoclonal antibodies against the human p55 TNF-R, which can mimic TNF action, different effects in transfectants with wild type or mutant receptors were observed. Cells transfected with the wild type human p55 TNF-R became highly sensitive to the cytotoxic action of these antibodies, which showed no effect on untransfected or control-transfected A9 cells. In contrast, transfectants expressing mutant receptors with deletion of the intracellular amino acids 405 to 426 of SEQ ID NO:2 were absolutely not responsive to antibodies against the human p55 TNF-R, in spite of similar levels of receptor expression. Still, these cells could respond to human TNF acting via the endogenous murine receptors for TNF, proving that the insensitivity was not due to a post-receptor blockade in the signal transduction pathway.

Receptor mutants (del: 415–426 of SEQ ID NO:2), with a deletion 10 amino acids shorter than in the aforementioned mutant, however, conferred to the transfected cells high responsiveness to the cytocidal action of antibodies against the human p55 TNF-R.

The above shows that amino acids 405 to 414 of SEQ ID NO:2, or part of them, are essential for the signaling of the human p55 TNF-R for the cytotoxic effect of TNF, whereas amino acids 415 to 426 of SEQ ID NO:2 are not essential.

In a third mutant, a single serine residue (amino acid 197) in the transmembrane domain was exchanged by site directed mutagenesis against alanine, an amino acid said to be compatible with all known secondary structures of amino acid sequences. Functional analysis of cells transfected with this receptor mutant revealed a significant impairment in these receptors to trigger cell death in response to mimetic antibodies against the human p55 TNF-R. Yet this functional disruption was not complete and a small cytocidal effect could still be observed.

Yet other mutants, in which either amino acids 170–174 of SEQ ID NO:2, 175–179 of SEQ ID NO:2 or both, i.e., amino acids 170–179 of SEQ ID NO:2, were deleted, abolished shedding of the soluble extracellular forms of the receptor. This finding demonstrates that the region of amino acids 170–179 of SEQ ID NO:2 or part thereof, of the receptor, which lies just outside the transmembrane domain, must be intact in order to allow formation of the soluble TNF receptors. Therefore, any interference with this region, or the effector protein interacting therewith, will abolish shedding. The effector protein, in this case, is believed to be a proteolytic enzyme.

As stated above, the present invention provides, amongst others, peptides and other molecules which can interact either with the receptor itself, or a certain region thereof, or with effector proteins interacting with the receptor, and to methods for the production of these peptides and substances.

For this purpose, proteins which interact with the relevant regions of the receptor are isolated from cellular extracts, e.g., by ligand affinity purification using these regions as ligands. Thereafter screening is carried out for substances which bind either with the receptor or with those isolated effector proteins, thus interfering with their interaction with each other. Such screening is effected in any one of the following ways:

1) Target peptides which correspond to the amino acid regions of the TNF-R found to be critical for signal transduction and/or shedding are synthesized and peptide libraries are screened for ligands which bind thereto. The peptides which bind to these regions are further screened for those which also bind to TNF-R. Finally, the peptides capable of high affinity binding with both the target peptides and the TNF-R, are screened for the ability of the peptide to perform the desired biological activity, i.e., influence the normal functioning of TNF-R.

2) In a similar manner, a variety of organic molecules, including drugs known for other indications, are screened for their ability to interfere with the normal functioning of TNF-R. This is determined by examining whether these molecules can bind or interact in a different manner with the amino acids or amino acid regions found to be critical for signal transduction and/or shedding of the TNF-R.
3) In addition to the organic molecules, also broth of biological matter, such as bacteria culture products, fungi culture products, eukaryotic culture products and crude cytokine preparations are screened with the amino acid target peptides described above. Molecules obtained by this screening are then further screened for their ability to perform the desired biological function.

In the same manner, effector proteins obtained, e.g., by chromatography of all extracts through a resin to which the target peptides were linked, are employed for screening of the above peptide libraries, organic molecules and biological broths. The molecules found in this manner to bind to the effector proteins are then examined for their ability to inhibit the interaction between the effector proteins and the TNF-R and thus for their ability to interfere with the normal functioning of the TNF-R.

Alternatively, molecules are designed which spatially fit the quaternary structure of the amino acid regions in the receptor or the effector protein, and thus interfere with the interaction of the two.

The active molecules obtained by the above procedures, insofar as they are biological substances, can also be prepared by biotechnological approaches. In this way, massive production of these molecules will be made possible. Peptides may either be produced by known peptide synthesis methods or using expression vectors containing DNA sequences encoding them. Other molecules, if produced in an enzymatic way, can be made by producing the enzymes involved in the appropriate cultured cells.

Pharmaceutical compositions containing the peptides or other molecules of the present invention may be employed for either antagonizing the deleterious effect of TNF in mammals, i.e., for treating conditions where excess TNF is either endogenously formed or exogenously administered, or for augmenting the beneficial effects of TNF, i.e., in the treatment of tumors.

Such compositions comprise the active peptides or other molecules according to the invention as their active ingredient. The pharmaceutical compositions are indicated for any conditions of excess TNF, such as in septic shock, cachexia, graft-versus-host reactions, autoimmune diseases such as rheumatoid arthritis, and the like. They are also indicated for counteracting, e.g., an overdose of exogenously administered TNF.

The pharmaceutical compositions according to the invention are administered depending on the condition to be treated, via the accepted ways of administration. For example, in the case of septic shock, intravenous administration will be preferred, while in the case of arthritis, local injection may be indicated. The pharmaceutical compositions may also be administered continuously, i.e., by way of infusion, or orally. The formulation and dose will depend on the condition to be treated, the route of administration and the condition and the body weight of the patient to be treated. The exact dose will be determined by the attending physician.

The pharmaceutical compositions according to the invention are prepared in the usual manner, for example by mixing the active ingredient with pharmaceutically and physiologically acceptable carriers and/or stabilizers and/or excipients, as the case may be, and are prepared in dosage form, e.g., by lyophilization in dosage vials.

The following examples illustrate the invention without limiting it thereto:

EXAMPLE 1

Construction of Mutant p55 TNF Receptors

Figure 3:
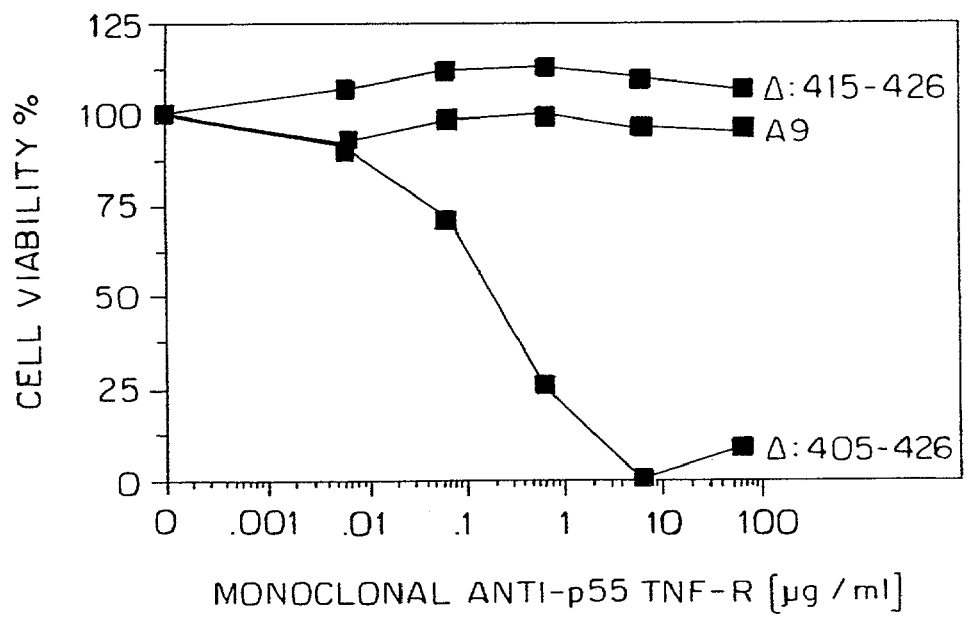
FIG. 3 demonstrates that the mutant of the p55 TNF-R in which amino acids 415–426 of SEQ ID NO:2 were deleted can still signal for a cytocidal effect while the mutant Δ: 405–426, from which an additional 10 amino acids were deleted, cannot.
Figure 4:
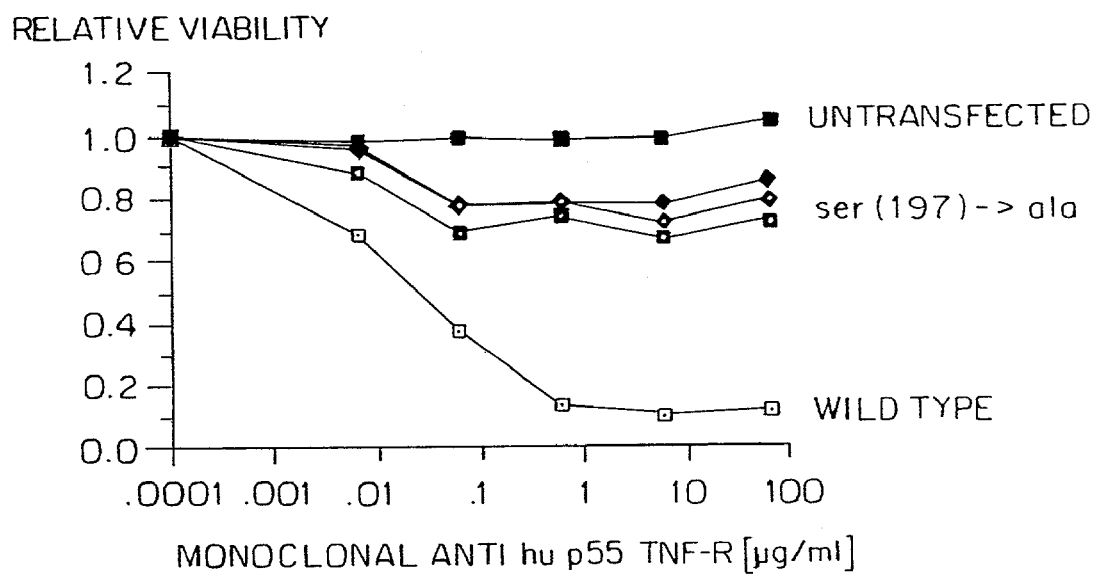
FIG. 4 shows that a mutant of p55 TNF-R in which $197_{ser}$ was replaced by ala has decreased ability to transduce the signal for the cytocidal effect.
Figure 5:
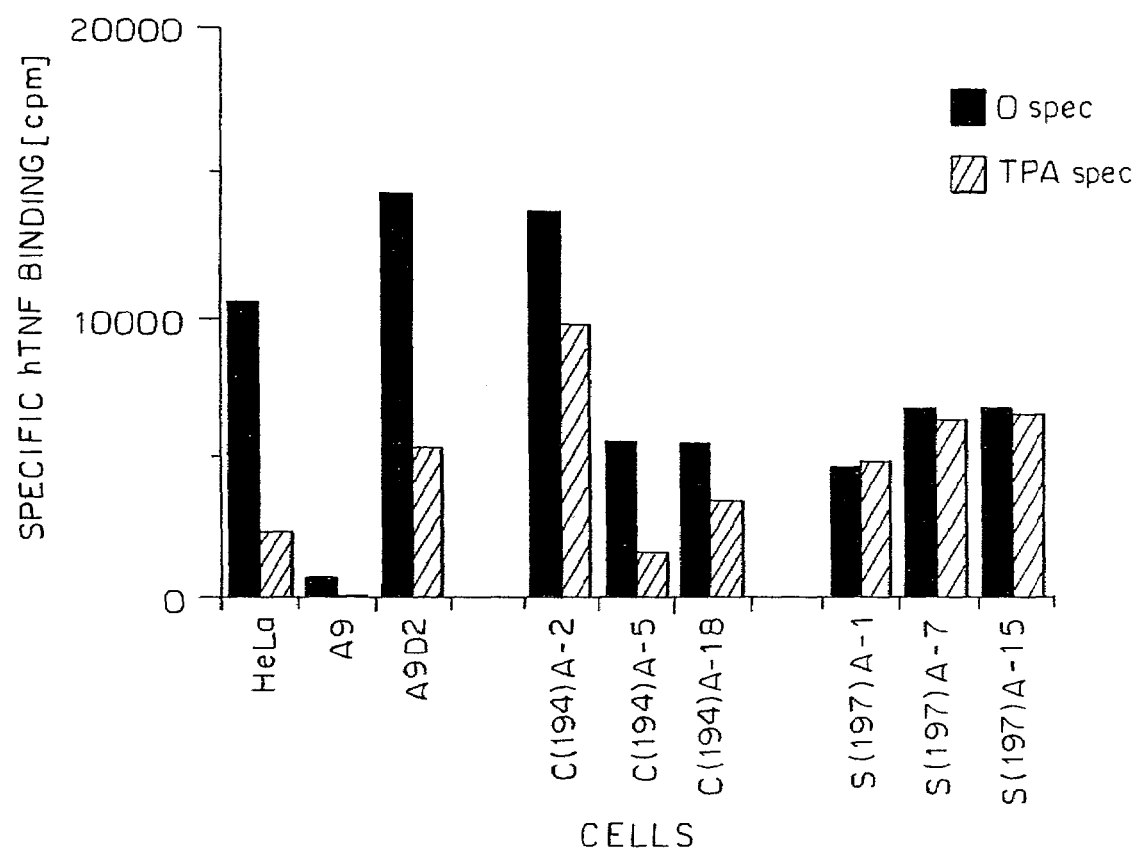
FIG. 5 demonstrates that the mutation in which $197_{ser}$ was replaced by ala abolishes the inducible shedding of the extracellular part of the p55 TNF-R.
Figure 6A:
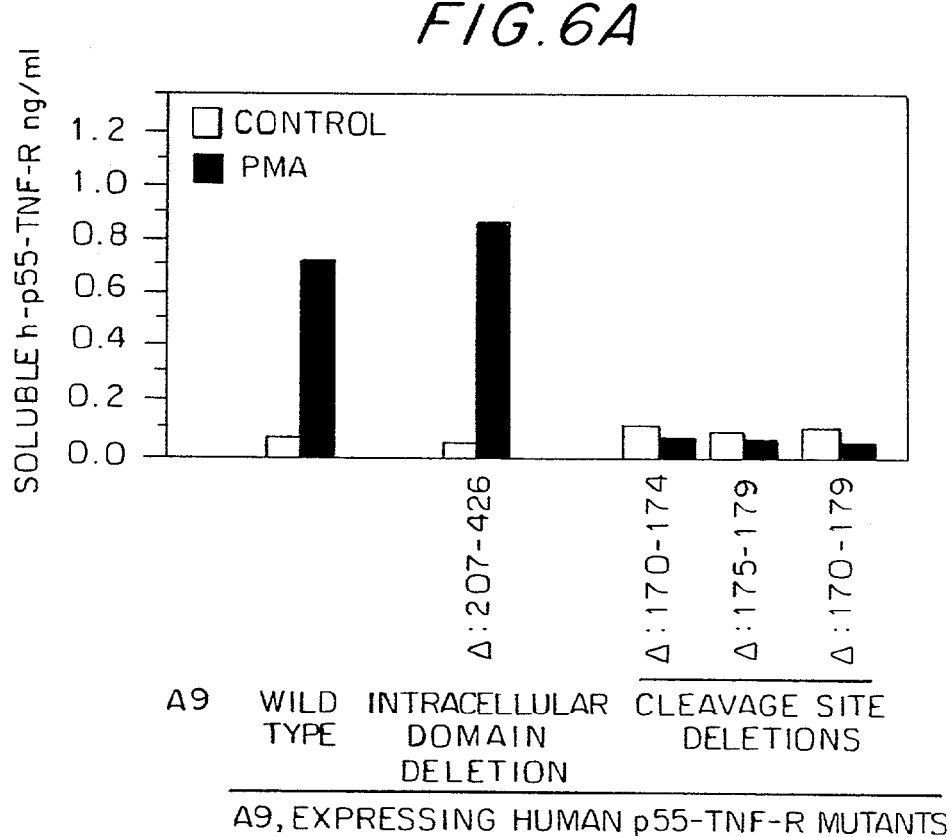
FIGS. 6A and 6B demonstrate that deletion of either amino acids 170–174 or 175–179 of SEQ ID NO:2, as well as deletion of all amino acids 170–179 of SEQ ID NO:2 abolishes the inducible shedding of the extracellular portion of the p55 TNF-R.
Figure 6B:
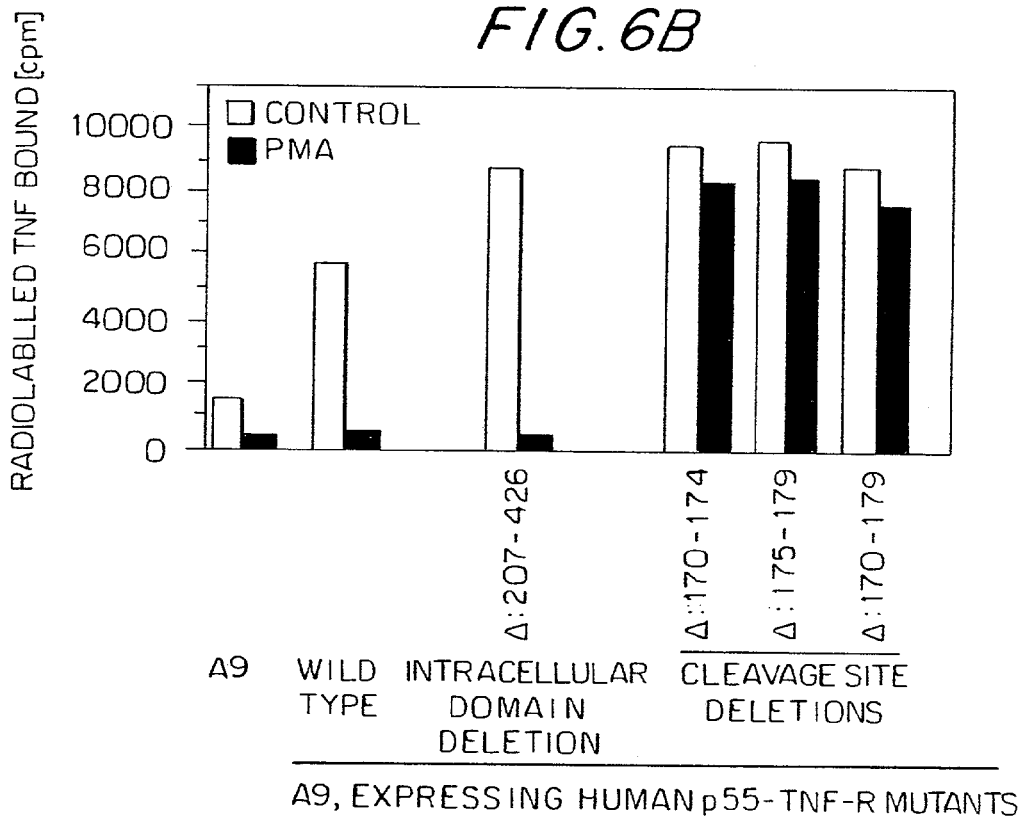

The cDNA of the human p55 TNF-R (Nophar et al, 1990) was digested with the BanII and NheI restriction enzymes, resulting in removal of large parts of the 5' and 3' non-coding regions. Mutants Δ: 405–426 and Δ: 415–426 (FIG. 3) were generated by oligonucleotide directed mutation of this shortened form of the cDNA, using the "Altered Sites" mutagenesis kit of Promega. Stop codons were introduced after cysteine 404 (mutant Δ: 405–426; amino acids in the receptor are numbered according to Loetscher et al, 1990), using the oligonucleotide 5' CTG CTG GGC TGC TAG CCT GGA GGA CAT 3' (SEQ ID NO:3), and after glycine 414 (mutant Δ: 416–426), using the oligonucleotide 5' AAG CCC TTT GCG GCT AGC CCC GCC GCC CT 3' (SEQ ID NO:4). Other mutants of the cDNA were produced similarly using the appropriate oligonucleotides to direct the desired mutations for the remaining mutants examined. The wild type and mutated cDNAs were introduced into the eukaryotic expression vector pMPSVEH (Artelt et al, 1988), which contains the myeloproliferative sarcoma virus promoter, an SV40 intron and the SV40 polyadenylation signal.

EXAMPLE 2

Expression of the Wild Type and the Mutant Receptors in Cultured Cells

Cells of the murine A9 line were cultured with Dulbecco's modified Eagle's Medium (DMEM), containing 10% fetal calf serum, 100 units/ml penicillin and 100 μg/ml streptomycin (growth medium). The cells were transfected with the expression constructs encoding the wild type and the mutant receptors, together with the neomycin resistance-conferring plasmid pSV2neo, using the calcium phosphate precipitation method (Graham and van der Eb, 1973). After 10 to 14 days selection in growth medium containing 500 μg/ml G418 (Sigma), resistant colonies were isolated and examined for expression of the human p55 TNF-R (hu-p55-TNF-R) by measuring TNF binding to the cells. Of all transfectants at least three different clones were analyzed in the functional assays to check for clone-to-clone variations of their properties.

EXAMPLE 3

Determination of TNF Binding to Cells

Recombinant human TNF-R (TNF, $6\times10^7$ units/mg of protein), produced by Genentech Co., San Francisco, Calif., was kindly provided by Dr. G. Adolf of the Boehringer Institute, Vienna, Austria. The TNF was radiolabeled with chloramine T to a specific radioactivity of 2000 mCi/mmol (Israel et al, 1986). To determine the binding of TNF, cells were seeded into 15 mm tissue culture plates at a density of $2.5\times10^5$ cells/plate. After 24 hours incubation at 37° C., the plates were transferred to ice, the growth medium was removed, and radiolabeled TNF was applied at a concentration of 0.1 nM, either alone or with a 1000-fold excess of unlabeled TNF, in 200 μl PBS (0.154 sodium chloride plus 10 mM sodium phosphate, pH 7.4) containing 1 mM $CaCl_2$, 1 mM $MgCl_2$, 0.5% BSA and 0.02% $NaN_3$ (binding buffer). After 3 hours of incubation on ice, the cells were rinsed and then detached by incubation in PBS containing 5 mM EDTA. Cell-bound radioactivity was determined in a gamma-counter.

EXAMPLE 4

Quantitation of the Cytocidal Effect of TNF and of Antibodies to the hu-D55-TNF-R Cells were seeded into 96 well plates, 24 hours before the assay at a density of 30,000 cells per well. The growth medium was then exchanged with 100 μl growth medium containing cycloheximide (CHI, 25 μg/ml for the HeLa cells and 50 μg/ml for all other cell types) and human TNF-R or monoclonal antibodies against the human p55 TNF-R (Engelmann et al, 1990b). After further 11 hours of incubation at 37° C., viability of the cells was assessed in a neutral red uptake assay as described before (Wallach, 1984).

EXAMPLE 5

Isolation of Effector Proteins by Ligand Affinity Purification

Synthetic peptides whose sequences correspond to those regions in the receptors found critical for signaling or cleavage are linked to a solid resin, e.g., Sepharose, Agarose or acrylamide hydrazide agarose or the like, by a covalent linker such as glutaraldehyde. Extracts of cells or cell membranes are applied to such a column and proteins binding to them eluted, e.g., by reduction of the pH. The fractions containing the proteins are collected and further purified according to conventional methods. The protein may be further purified. In this further purification, the proteins can be followed by determination of their specific activity (proteolytic or signaling).

EXAMPLE 6

Preparation of Antibodies or Fragments Thereof which Interact with the TNF-R or with the Effector Proteins The TNF-R or regions in it found to be critical for its function, or purified effector proteins interacting with them are injected into mice, rabbits or other suitable animals commonly used for development of antibodies using appropriate protocols. Monoclonal antibodies are developed against the above proteins using spleens of the immunized animals in the usual manner. DNA extracted from the spleen cells or from hybridomas developed therefrom are used to produce the antibodies by recombinant DNA technologies. In this manner, antibodies which modulate the function of TNF, either by interfering with its signal transduction or with the cleavage of the receptor, are obtained.

Using the DNA which encodes the antibodies, smaller molecules with the same binding activity whose structure corresponds to the hypervariable regions in the antibodies and derivatives thereof, are constructed. These molecules are designed in a manner which allows them also to penetrate the cell membranes in order to interact with the cytoplasmic domain of the receptors or with cytoplasmic effector proteins.

EXAMPLE 7

Identification of Organic Molecules or of Other Components of Biological Broths which Interfere with Receptor-Effector Proteins Interactions Effector proteins isolated and purified as in Example 5 are labeled, e.g., with $^{125}$I or another radioactive tracer or with a fluorescent marker, and the effectivity of their interaction with solid phase bound receptor molecules or fragments thereof is measured in the presence of various biological broths or synthetic organic molecules in order to identify a molecule or molecules, which are capable of interfering with this interaction. By the same method such molecules can be followed in their purification from the crude preparations.

EXAMPLE 8

Preparation of a Neotide Capable of Interfering With the Function of TNF-R (Signal Transduction or Shedding)

A. Synthesis of Target Peptides

The target peptides have the following sequences:

```
Peptide A:  Ile Glu Asn Val Lys            SEQ ID NO:5

Peptide B:  Gly Thr Gln Asp Ser            SEQ ID NO:6
```

-continued

```
Peptide C:  Ile Glu Asn Val Lys Gly Thr    SEQ ID NO:7
            Gln Asp Ser Peptide D:  Leu Glu Asp Ile Glu Glu Ala    SEQ ID NO:8
            Leu Cys Gly
```

Peptide A corresponds to amino acids 170–174 of SEQ ID NO:2, peptide B to amino acids 175–179 of SEQ ID NO:2, peptide C to amino acids 170–179 of SEQ ID NO:2, and peptide D to amino acids 405–414 of SEQ ID NO:2 of the amino acid sequence of TNF-R as shown in FIG. 1.

The target peptides are synthesized using Fmoc protected amino acid derivatives, according to the usual procedures, e.g. according to Chang and Meienhoffer (1978); Grandas et al (1989); Fournier et al (1989); Stewart and Young (1984); or similar methods.

B. Synthesis of Combinatorial Peptide Library Beads And Linkers

The combinatorial peptide library is synthesized on suitable bead carriers, e.g., beads made of polystyrene crossed with divinyl benzene (1% DVB), diameter about 200 microns, containing about 1 mili-equivalent of binding site, e.g., primary amines, or acid labile chloromethyl group. Linkers, such as cystamine, can be coupled to the beads by using a suitable cross linker, e.g., glutardialdehyde. Peptide synthesis is performed on the free amine of the cystamine. At the termination of the synthesis, the cystamine bridge is cleaved by mild reduction, e.g., by use of dithiothreitol, resulting in a peptide having a free C terminal SH group. This group, which in many peptides is unique, serves as a specific modification site for binding of a recognition molecule, e.g., by reaction with iminobiotin-maleimide.

Library Synthesis Strategy

Primary Library: The library synthesis strategy is designed to allow screening of peptides of sizes of 9 or more residues, and composed of up to about 100 different amino acid derivatives. The first 6 amino acids are randomly synthesized by incorporation of all the different amino acid derivatives into each synthesis cycle. In the last 3 synthesis cycles, a unique sequence of amino acids per bead is synthesized, as follows:

Following the incorporation of amino acid no. 6, the beads are aliquoted. The number of aliquots is identical to the number of different amino acid derivatives. A single amino acid derivative is then incorporated into the 7th position of growing polypeptide chain of all the beads in a single aliquot. The beads are then mixed together, and redistributed as before. This procedure is repeated 3 times, resulting in incorporation of a total of 3 unique amino acid residues per bead. This format of synthesis is called "structured synthesis" to differentiate from the random synthesis format used to synthesize the peptide in positions 1–6.

The primary library is then screened as described below. The results of the screening allow selection of specific tripeptide sequences capable of binding to the target sequences.

Secondary Library: Synthesis of the secondary library is performed after the appropriate tripeptide sequence(s) are identified by screening of the primary library. The synthesis of the secondary library is carried out similarly to the synthesis of the primary library in concept. The first 3 amino acid residues are randomly synthesized, the next 3 amino acid residues are synthesized by structured synthesis, and the last 3 amino acids are synthesized according to the sequence(s) derived from screening of the primary library.

Tertiary Library: The tertiary library is synthesized similarly to the primary and secondary libraries in concept. The first 3 amino acid residues are synthesized by structured synthesis, and the final 6 amino acid residues are incorporated according to the sequence(s) derived from screening of the primary and secondary libraries.

C. Extended Synthesis/Screening Process

The process described above results in identification of peptides composed of 9 amino acid residues, which are capable of binding specifically to the target ligands. It is possible to continue the synthesis/screening process in order to prepare longer peptides, which might perform better. It may also be advantageous to further modify the peptide, e.g., stabilize the peptide conformation by cross-linking of side chains, protect against proteolytic cleavage by modification of the peptide bond, increase potential for transmembrane transport by conjugation of hydrophobic residues to side chains, etc., in order to improve its activity. It is then possible to carry out the modifications according to the above strategy. This approach allows fast screening of many modified peptides and greatly reduces the time needed in order to identify the desired peptide.

D. Screening of the Library

The screening of the library (peptides) is divided into 2 phases:

Phase A: Screening for ligand binding, i.e., binding to the target peptide and to the native protein.

Phase B: Screening for the capability of the peptides to diminish or abolish TNF-R shedding in response to TNF, or to block signal transduction by the TNF-R.

Phase A: Screening for Ligand Binding Potential

The libraries are exposed to the ligand, e.g., any of the target peptides indicated above or the purified TNF-R. Detection of the bound ligand is possible following direct labeling of the ligand, e.g., by labeling with a fluorescent dye, such as tetramethyl rhodamine, or by using specific polyclonal antibodies and an appropriate second antibody coupled to a suitable marker, e.g., the enzyme alkaline phosphatase or horseradish peroxidase. The bound enzyme is detected using an appropriate substrate, e.g., for alkaline phosphatase BCIP coupled with a tetrazolium salt such as nitroblue tetrazolium, or for horseradish peroxidase chloronaphtol or tetramethyl benzidine.

Detection of beads which bind the ligand is effected either by monitoring bead fluorescence, e.g., by using a FACS machine, or by monitoring bead color by visual inspection. The labeled beads are retrieved from the mixture and the peptides of individual beads are sequenced by automatic peptide sequencer. The sequence data obtained enable designing of further libraries.

After detection of beads which bind to the target peptide, their binding to the protein carrying the target peptide is confirmed. This is carried out using a process similar to the one used for determination of the binding of the target peptide, but using highly purified TNF-R as ligand.

Phase B: Screening for Bioactivity

After identification of peptides capable of high affinity binding with the target peptides and to the TNF-R through the library screening cycles described above has been effected, screening for the ability of the peptide to perform the desired biological activity is carried out. Here we distinguish between peptides which are expected to operate outside of the cell (the peptide intended to block the TNF-R shedding) and peptides which are intended to operate inside the cytoplasm, such as those intended to block the signal transduction by the TNF-R.

EXAMPLE 9

Screening for Peptides Intended for Elimination of TNF-R Shedding

All peptides capable of binding to the target peptides A, B or C and to the extracellular domain of the TNF-R are tested for their ability to reduce shedding of the TNF-R in response to TNF.

Cells are reacted with a mixture of peptides capable of binding to the extracellular domain of the TNF-R. Following incubation, the cells are lysed and the TNF-R molecules are purified by immunoaffinity on an appropriate McAb. It is assumed that only those TNF-R molecules would remain at the cell surface whose shedding was prevented by the respective peptides. Thus, the purified TNF-R molecules are expected to carry those inhibiting peptides. The peptides are purified from the purified TNF-R preparation, and sequenced. Alternatively, the desired peptides are eluted directly from the cells themselves, obviating the need to purify the TNF-R. Since the TNF-R is shed from the cells by cleavage at a site which is very close to the cell membrane, it is expected that all the peptides which bind at sites distant from the cleavage site would be removed from the cell surface together with the shed TNF-R segment. The peptides extracted from the cells are purified by SEC-HPLC or alternatively the peptides are labeled with iminobiotin (as described above) and purified by affinity chromatography using avidin columns.

EXAMPLE 10

Screening of Peptides Intended for Inhibition of Signal Transduction by the TNF-R Screening for peptides capable of inhibiting signal transduction by the TNF-R is more complicated. The major obstacle for the ability of the peptides to interfere with the signal transducing capability of the TNF-R, is their need to cross the cell membrane and accumulate . . . high enough concentration in the cytoplasm of the target cell.

The screening therefore has to be divided. In the initial screening, performed as described above, peptides are tested for the ability of the peptides (on beads) to bind to the target peptides and to the purified intracellular domain of the TNF-R molecule. Those peptides capable of binding are screened for their ability to block the signal transduction by the TNF-R. In order to facilitate the transport of the peptide through the membrane and into the cytoplasm, the peptides are chemically modified on the beads, e.g., (1) by oxidation of methionine to sulfoxide, (2) by replacing the peptide bond with its ketomethylene isoester ($COCH_2$) (Zacharia et al, 1991); (3) by introduction of lauroyl derivatives (Muranishi et al, 1991).

Modification of the peptides is carried out when the peptides are on the beads. The modified peptides are screened for their ability to bind to the intracellular domain of the TNF-R. Those peptides which retain the ability to bind to the TNF-R are cleaved from the beads and are further tested using live cells expressing the TNF-R for their ability to pass the membrane and block the TNF-R signal transduction.

EXAMPLE 11

Creation of Inhibitors of Signaling and Cleavage Which Spatially Fit the Regions of the TNF-Rs Found Critical for Function The 3-dimensional structure of the TNF-R is determined by X-ray crystallography of crystals produced thereof. Special attention must be given to the structure of the regions found by the mutation analysis (FIGS. 3 to 6) to be critical for the signaling or cleavage of the receptor. Three-dimensional structures of known molecules are compared to the structures conceived by the above analysis in order to complement the structure of those critical regions. Molecules found in this way to resemble the derived complementary structure are examined for their ability to interfere with the signaling or cleavage of the receptors. If found to have any sign for effect, these molecules are modified by creating derivatives thereof in order to further approach the desired complementary structures. In such sequential modification besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the peptides or other molecules of the invention and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama et al (1983).

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli,* for example, pBR322, ColEl, pSC101, pACYC 184, etc. (see Maniatis et al, 1982); Bacillus plasmids such as pC194, pC221, pT127, etc. (Gryczan, , 1982); Streptomyces plasmids including pIJ101 (Kendall et al, 1987); Streptomyces bacteriophages such as ØC31 (Chater et al, 1986), and Pseudomonas plasmids (John et al, 1986; and Izaki, 1978).

Preferred eukaryotic plasmids include BPV, vaccinia, SV40, 2-micron circle, etc., or their derivatives. Such plasmids are well known in the art (Botstein et al, 1982; Broach, 1981; Broach, 1982; Bollon et al, 1980; Maniatis, 1980).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc.

Host cells to be used in this invention may be either prokaryotic or eukaryotic. Preferred prokaryotic hosts include bacteria such as *E. coli, Bacillus, Streptomyces, Pseudomonas, Salmonella, Serratia,* etc. The most preferred prokaryotic host is *E. coli.* Bacterial hosts of particular interest include *E. coli* K12 strain 294 (ATCC 31446), *E. coli* X1776 (ATCC 31537), *E. coli* W3110 (F$^-$, lambda$^-$, prototropic (ATCC 27325)), and other enterobacterium such as Salmonella typhimurium or Serratia marcescens and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and Chinese hamster ovary (CHO) cells, because they provide post-translational modifications to protein molecules including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector, the host cells are grown in a selective medium, which selects for the growth of vector-containing cells. Expression of the cloned gene sequence(s) results in the production of the desired proteins.

Purification of the recombinant proteins is carried out by any one of the methods known for this purpose.

Although reference is made throughout to the p55-TNF-R, it is evident from what is known of the p75-TNF-R, that it functions similarly. Therefore the present invention encompasses modulation of the signal transduction and/or cleavage in both known TNF receptors.

REFERENCES

Aggarwal et al, "Characterization of receptors for human tumour necrosis factor and their regulation by gamma-interferon", *Nature* 318(6047):665–667 (1985)

Artelt et al, "Vectors for efficient expression in mammalian fibroblastoid, myeloid and lymphoid cells via transfection or infection", *Gene* 68(2):213–219 (1988)

Baglioni et al, "Binding of human tumor necrosis factor to high affinity receptors on HeLa and lymphoblastoid cells sensitive to growth inhibition", *J Biol Chem* 260(25): 13395–13397 (1985)

Beutler and Cerami, "The biology of cachectin/TNF—a primary mediator of the host response", *Annul Rev Immunol* 7:625–655 (1989)

Beutler et al, "Purification of cachectin, a lipoprotein lipase-suppressing hormone", secreted by endotoxin-induced RAW 264.7 cells *J Exp Med* 161:984–995 (1985)

Bollon DP et al *J Clin Hematol Oncol* 10:39–48 (1980)

Botstein D et al Miami Wint Symp 19, pp. 265–274 (1982)

Broach J R in *The Molecular Biology of the Yeast Saccharomyces: Life Cycle and Inheritance,* Cold Spring Harbor Laboratory, Cold Spring Harbor, N.Y., pp. 445–470 (1981)

Broach J R, "The yeast plasmid 2 mu circle", *Cell,* 28(2): 203–204 (1982)

Brockhaus et al, "Identification of two types of tumor necrosis factor receptors on human cell lines by monoclonal antibodies", *Proc Nat Acad Sci USA* 87(8):3127–3131 (1990)

Chang and Meienhoffer, "Solid-phase peptide synthesis using mild base cleavage of N alpha-fluorenylmethyloxycarbonylamino acids, exemplified by a synthesis of dihydrosomatostatin", *Int J of Peptide Protein Res* 11:246–249 (1978)

Chater et al, in Sixth International Symposium on Actinomycetales Biology, Akademiai Kaido, Budapest, Hungary pp. 45–54 (1986)

Engelmann et al, "Antibodies to a soluble form of a tumor necrosis factor (TNF) receptor have TNF-like activity", *J Biol Chem* 265(24):14497–14504 (1990a)

Engelmann et al, "Two tumor necrosis factor-binding proteins purified from human urine. Evidence for immunological cross-reactivity with cell surface tumor necrosis factor receptors", *J Biol Chem* 265(3):1531–1536 (1990b)

Fournier A et al, *Int J Peptide Protein Res* 33:133–139 (1989)

Glick B R, *J Ind Microbiol* 1:277–282 (1987)

Graham and van der Eb, "A new technique for the assay of infectivity of human adenovirus 5 DNA", *Virology* 52(2): 456–467 (1973)

Grandas A et al, *Tetrahedron* 45:4637–4648 (1989)

Gryczan T, *The Molecular Biology of the Bacilli,* Academic Press, N.Y., pp. 307–329 (1982)

Israel et al, "Binding of human TNF-alpha to high-affinity cell surface receptors: effect of IFN" *Immunol Lett* 12(4): 217–224 (1986)

Izaki K, "Plasmid-determined resistance to heavy metals (author's transl)" *Jpn J Bacteriol* 33(6):729–742 (1978)

John et al, "Plasmids as epidemiologic markers in nosocomial gram-negative bacilli: experience at a university and review of the literature", *Rev Infect Dis* 8(5):693–704 (1986)

Kendall et al, "Plasmid transfer in Streptomyces lividans: identification of a kil-kor system associated with the transfer region of pIJ101", *J Bacteriol* 169(9):4177–4183 (1987)

Kull et al, "Cellular receptor for 125I-labeled tumor necrosis factor: specific binding, affinity labeling, and relationship to sensitivity", *Proc Nat Acad Sci USA* 82(17):5756–5760 (1985)

Loetscher et al, "Purification and partial amino acid sequence analysis of two distinct tumor necrosis factor receptors from HL60 cells", *J Biol Chem* 265(33):20131–20138 (1990)

Maniatis T et al, *Molecular Cloning: A Laboratory Manual,* Cold Spring Harbor Laboratory, Cold Spring Harbor (1982).

Maniatis T, in: *Cell Biology: A Comprehensive Treatise. Vol. 3: Gene Expression,* Academic Press, N.Y., pp. 563–608 (1980)

Muranishi et al, "Lipophilic peptides: synthesis of lauroyl thyrotropin-releasing hormone and its biological activity", *Pharmaceutical Res,* 8(5):649–652 (1991)

Nophar et al, "Soluble forms of tumor necrosis factor receptors (TNF-Rs). The cDNA for the type I TNF-R, cloned using amino acid sequence data of its soluble form, encodes both the cell surface and a soluble form of the receptor", *EMBO J* 9(1):3269–3278 (1990)

Okayama et al, "A cDNA cloning vector that permits expression of cDNA inserts in mammalian cells", *Mol Cell Biol* 3(2):280–289 (1983)

Old L J, in: *Tumor Necrosis Factor: Structure, Mechanism of Action, Role of Disease and Therapy,* Bonavida et al (eds.), Karger, Basel, pp. 1–30 (1990)

Porteu and Nathan, "Shedding of tumor necrosis factor receptors by activated human neutrophilsd", *J Exp Med* 172(2):599–607 (1990)

Porteu et al, "Human neutrophil elastase releases a ligand-binding fragment from the 75-kDa tumor necrosis factor (TNF) receptor. Comparison with the proteolytic activity responsible for shedding of TNF receptors from stimulated neutrophils", *J Biol Chem* 266(28):18846–18853 (1991)

Stewart M J and Young J D, *Solid phase peptide synthesis,* Pierce Chemical Company (1984)

Tsujimoto et al, "Tumor necrosis factor: specific binding and internalization in sensitive and resistant cells", *Proc Nat Acad Sci USA* 82(22):7626–7630 (1985)

Wallach D, "Preparations of lymphotoxin induce resistance to their own cytotoxic effect", *J Immunol* 132(5):2464–2469 (1984)

Zacharia et al, "New reduced peptide bond substance P agonists and antagonists: effects on smooth muscle contraction", *Eur J of Pharmacol* 203(3):353–357 (1991)

What is claimed is:

1. An isolated molecule that inhibits the cleavage of the soluble form of p55-TNF-R from the p55-TNF-R, comprising an antibody or fragment thereof, which antibody or fragment binds to the human p55-TNF-R in the region of amino acids 170–174, 175–179 or 170–179 of human p55-TNF-R (SEQ ID NO:2) in such a manner that cleavage of the soluble form of p55-TNF-R from the p55-TNF-R is inhibited.

2. An isolated molecule in accordance with claim 1, comprising an antibody that binds to the human p55-TNF-R in the region of amino acids 170–174, 175–179 or 170–179 of human p55-TNF-R (SEQ ID NO:2) in such a manner that cleavage of the soluble form of p55-TNF-R from the p55-TNF-R is inhibited.

3. An isolated molecule in accordance with claim 1, comprising a fragment of an antibody, which fragment and antibody bind to the human p55-TNF-R in the region of amino acids 170–174, 175–179 or 170–179 of human p55-TNF-R (SEQ ID NO:2) in such a manner that cleavage of the soluble form of p55-TNF-R from the p55-TNF-R is inhibited.

4. An isolated molecule in accordance with claim 1, consisting of an antibody that binds to the human p55-TNF-R in the region of amino acids 170–174, 175–179 or 170–179 of human p55-TNF-R (SEQ ID NO:2) in such a manner that cleavage of the soluble form of p55-TNF-R from the p55-TNF-R is inhibited.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
    (A) LENGTH: 2175 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 256..1620

(xi) SEQUENCE DESCRIPTION: SEQ ID NO: 1:

```
CGGCCCAGTG ATCTTGAACC CCAAAGGCCA GAACTGGAGC CTCAGTCCAG AGAATTCTGA    60

GAAAATTAAA GCAGAGAGGA GGGGAGAGAT CACTGGGACC AGGCCGTGAT CTCTATGCCC   120

GAGTCTCAAC CCTCAACTGT CACCCCAAGG CACTTGGGAC GTCCTGGACA GACCGAGTCC   180

CGGGAAGCCC CAGCACTGCC GCTGCCACAC TGCCCTGAGC CCAAATGGGG GAGTGAGAGG   240

CCATAGCTGT CTGGC ATG GGC CTC TCC ACC GTG CCT GAC CTG CTG CTG CCG   291
                Met Gly Leu Ser Thr Val Pro Asp Leu Leu Leu Pro
                  1               5                  10

CTG GTG CTC CTG GAG CTG TTG GTG GGA ATA TAC CCC TCA GGG GTT ATT   339
Leu Val Leu Leu Glu Leu Leu Val Gly Ile Tyr Pro Ser Gly Val Ile
            15                  20                  25

GGA CTG GTC CCT CAC CTA GGG GAC AGG GAG AAG AGA GAT AGT GTG TGT   387
Gly Leu Val Pro His Leu Gly Asp Arg Glu Lys Arg Asp Ser Val Cys
 30                  35                  40

CCC CAA GGA AAA TAT ATC CAC CCT CAA AAT AAT TCG ATT TGC TGT ACC   435
Pro Gln Gly Lys Tyr Ile His Pro Gln Asn Asn Ser Ile Cys Cys Thr
 45                  50                  55                  60

AAG TGC CAC AAA GGA ACC TAC TTG TAC AAT GAC TGT CCA GGC CCG GGG   483
Lys Cys His Lys Gly Thr Tyr Leu Tyr Asn Asp Cys Pro Gly Pro Gly
                 65                  70                  75

CAG GAT ACG GAC TGC AGG GAG TGT GAG AGC GGC TCC TTC ACC GCT TCA   531
Gln Asp Thr Asp Cys Arg Glu Cys Glu Ser Gly Ser Phe Thr Ala Ser
             80                  85                  90

GAA AAC CAC CTC AGA CAC TGC CTC AGC TGC TCC AAA TGC CGA AAG GAA   579
Glu Asn His Leu Arg His Cys Leu Ser Cys Ser Lys Cys Arg Lys Glu
         95                  100                 105

ATG GGT CAG GTG GAG ATC TCT TCT TGC ACA GTG GAC CGG GAC ACC GTG   627
Met Gly Gln Val Glu Ile Ser Ser Cys Thr Val Asp Arg Asp Thr Val
    110                 115                 120

TGT GGC TGC AGG AAG AAC CAG TAC CGG CAT TAT TGG AGT GAA AAC CTT   675
Cys Gly Cys Arg Lys Asn Gln Tyr Arg His Tyr Trp Ser Glu Asn Leu
125                 130                 135                 140

TTC CAG TGC TTC AAT TGC AGC CTC TGC CTC AAT GGG ACC GTG CAC CTC   723
Phe Gln Cys Phe Asn Cys Ser Leu Cys Leu Asn Gly Thr Val His Leu
                145                 150                 155

TCC TGC CAG GAG AAA CAG AAC ACC GTG TGC ACC TGC CAT GCA GGT TTC   771
Ser Cys Gln Glu Lys Gln Asn Thr Val Cys Thr Cys His Ala Gly Phe
            160                 165                 170

TTT CTA AGA GAA AAC GAG TGT GTC TCC TGT AGT AAC TGT AAG AAA AGC   819
Phe Leu Arg Glu Asn Glu Cys Val Ser Cys Ser Asn Cys Lys Lys Ser
        175                 180                 185

CTG GAG TGC ACG AAG TTG TGC CTA CCC CAG ATT GAG AAT GTT AAG GGC   867
Leu Glu Cys Thr Lys Leu Cys Leu Pro Gln Ile Glu Asn Val Lys Gly
    190                 195                 200

ACT GAG GAC TCA GGC ACC ACA GTG CTG TTG CCC CTG GTC ATT TTC TTT   915
Thr Glu Asp Ser Gly Thr Thr Val Leu Leu Pro Leu Val Ile Phe Phe
205                 210                 215                 220
```

| | | |
|---|---|---|
| GGT CTT TGC CTT TTA TCC CTC CTC TTC ATT GGT TTA ATG TAT CGC TAC<br>Gly Leu Cys Leu Leu Ser Leu Leu Phe Ile Gly Leu Met Tyr Arg Tyr<br>                       225                   230                   235 | 963 |
| CAA CGG TGG AAG TCC AAG CTC TAC TCC ATT GTT TGT GGG AAA TCG ACA<br>Gln Arg Trp Lys Ser Lys Leu Tyr Ser Ile Val Cys Gly Lys Ser Thr<br>         240                   245                   250 | 1011 |
| CCT GAA AAA GAG GGG GAG CTT GAA GGA ACT ACT ACT AAG CCC CTG GCC<br>Pro Glu Lys Glu Gly Glu Leu Glu Gly Thr Thr Thr Lys Pro Leu Ala<br>         255                   260                   265 | 1059 |
| CCA AAC CCA AGC TTC AGT CCC ACT CCA GGC TTC ACC CCC ACC CTG GGC<br>Pro Asn Pro Ser Phe Ser Pro Thr Pro Gly Phe Thr Pro Thr Leu Gly<br>270                   275                   280 | 1107 |
| TTC AGT CCC GTG CCC AGT TCC ACC TTC ACC TCC AGC TCC ACC TAT ACC<br>Phe Ser Pro Val Pro Ser Ser Thr Phe Thr Ser Ser Ser Thr Tyr Thr<br>285                   290                   295                   300 | 1155 |
| CCC GGT GAC TGT CCC AAC TTT GCG GCT CCC CGC AGA GAG GTG GCA CCA<br>Pro Gly Asp Cys Pro Asn Phe Ala Ala Pro Arg Arg Glu Val Ala Pro<br>                       305                   310                   315 | 1203 |
| CCC TAT CAG GGG GCT GAC CCC ATC CTT GCG ACA GCC CTC GCC TCC GAC<br>Pro Tyr Gln Gly Ala Asp Pro Ile Leu Ala Thr Ala Leu Ala Ser Asp<br>         320                   325                   330 | 1251 |
| CCC ATC CCC AAC CCC CTT CAG AAG TGG GAG GAC AGC GCC CAC AAG CCA<br>Pro Ile Pro Asn Pro Leu Gln Lys Trp Glu Asp Ser Ala His Lys Pro<br>               335                   340                   345 | 1299 |
| CAG AGC CTA GAC ACT GAT GAC CCC GCG ACG CTG TAC GCC GTG GTG GAG<br>Gln Ser Leu Asp Thr Asp Asp Pro Ala Thr Leu Tyr Ala Val Val Glu<br>         350                   355                   360 | 1347 |
| AAC GTG CCC CCG TTG CGC TGG AAG GAA TTC GTG CGG CGC CTA GGG CTG<br>Asn Val Pro Pro Leu Arg Trp Lys Glu Phe Val Arg Arg Leu Gly Leu<br>365                   370                   375                   380 | 1395 |
| AGC GAC CAC GAG ATC GAT CGG CTG GAG CTG CAG AAC GGG CGC TGC CTG<br>Ser Asp His Glu Ile Asp Arg Leu Glu Leu Gln Asn Gly Arg Cys Leu<br>               385                   390                   395 | 1443 |
| CGC GAG GCG CAA TAC AGC ATG CTG GCG ACC TGG AGG CGG CGC ACG CCG<br>Arg Glu Ala Gln Tyr Ser Met Leu Ala Thr Trp Arg Arg Arg Thr Pro<br>         400                   405                   410 | 1491 |
| CGG CGC GAG GCC ACG CTG GAG CTG CTG GGA CGC GTG CTC CGC GAC ATG<br>Arg Arg Glu Ala Thr Leu Glu Leu Leu Gly Arg Val Leu Arg Asp Met<br>               415                   420                   425 | 1539 |
| GAC CTG CTG GGC TGC CTG GAG GAC ATC GAG GAG GCG CTT TGC GGC CCC<br>Asp Leu Leu Gly Cys Leu Glu Asp Ile Glu Glu Ala Leu Cys Gly Pro<br>         430                   435                   440 | 1587 |
| GCC GCC CTC CCG CCC GCG CCC AGT CTT CTC AGA TGAGGCTGCG CCCTGCGGGC<br>Ala Ala Leu Pro Pro Ala Pro Ser Leu Leu Arg<br>445                   450                   455 | 1640 |
| AGCTCTAAGG ACCGTCCTGC GAGATCGCCT TCCAACCCCA CTTTTTTCTG GAAAGGAGGG | 1700 |
| GTCCTGCAGG GGCAAGCAGG AGCTAGCAGC CGCCTACTTG GTGCTAACCC CTCGATGTAC | 1760 |
| ATAGCTTTTC TCAGCTGCCT GCGCGCCGCC GACAGTCAGC GCTGTGCGCG CGGAGAGAGG | 1820 |
| TGCGCCGTGG GCTCAAGAGC CTGAGTGGGT GGTTTGCGAG GATGAGGGAC GCTATGCCTC | 1880 |
| ATGCCCGTTT TGGGTGTCCT CACCAGCAAG GCTGCTCGGG GGCCCCTGGT TCGTCCCTGA | 1940 |
| GCCTTTTTCA CAGTGCATAA GCAGTTTTTT TTGTTTTTGT TTTGTTTTGT TTGTTTTTA | 2000 |
| AATCAATCAT GTTACACTAA TAGAAACTTG GCACTCCTGT GCCCTCTGCC TGGACAAGCA | 2060 |
| CATAGCAAGC TGAACTGTCC TAAGGCAGGG GCGAGCACGG AACAATGGGG CCTTCAGCTG | 2120 |
| GAGCTGTGGA CTTTTGTACA TACACTAAAA TTCTGAAGTT AAAAAAAAAA AAAAA | 2175 |

(2) INFORMATION FOR SEQ ID NO: 2:

(i) SEQUENCE CHARACTERISTICS:
       (A) LENGTH: 455 amino acids
       (B) TYPE: amino acid
       (D) TOPOLOGY: linear (ii) MOLECULE TYPE: protein (xi) SEQUENCE DESCRIPTION: SEQ ID NO: 2:

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
             20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
             100                 105                 110

Glu Ile Ser Ser Cys Thr Val Asp Arg Asp Thr Val Cys Gly Cys Arg
         115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365
```

```
Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
450                 455
```

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

CTGCTGGGCT GCTAGCCTGG AGGACAT                27

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AAGCCCTTTG CGGCTAGCCC CGCCGCCCT              29

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ile Glu Asn Val Lys
1               5

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Gly Thr Gln Asp Ser (2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Ile Glu Asn Val Lys Gly Thr Gln Asp Ser
1               5                   10
```

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Leu Glu Asp Ile Glu Glu Ala Leu Cys Gly
1               5                   10
```